United States Patent
Preissegger et al.

(10) Patent No.: US 11,883,532 B2
(45) Date of Patent: Jan. 30, 2024

(54) PHARMACEUTICAL COMPOSITIONS FOR PARENTERAL ADMINISTRATION COMPRISING IBUPROFEN AND A PHOSPHATE BUFFER

(71) Applicant: FRESENIUS KABI AUSTRIA GMBH, Graz (AT)

(72) Inventors: Patricia Preissegger, Graz (AT); Eva Trotscha, Graz (AT)

(73) Assignee: FRESENIUS KABI AUSTRIA GMBH, Graz (AT)

(*) Notice: Subject to any disclaimer, the term of this patent is extended or adjusted under 35 U.S.C. 154(b) by 195 days.

(21) Appl. No.: 17/346,824

(22) Filed: Jun. 14, 2021

(65) Prior Publication Data
US 2021/0369611 A1   Dec. 2, 2021

Related U.S. Application Data

(63) Continuation-in-part of application No. PCT/EP2019/085138, filed on Dec. 13, 2019.

(30) Foreign Application Priority Data

Dec. 14, 2018 (EP) .................... 18212668

(51) Int. Cl.
| | | |
|---|---|---|
| A61J 1/14 | (2023.01) | |
| A61K 31/192 | (2006.01) | |
| A61K 47/02 | (2006.01) | |
| C08L 23/06 | (2006.01) | |
| A61K 9/08 | (2006.01) | |
| A61K 9/00 | (2006.01) | |

(52) U.S. Cl.
CPC ............ *A61K 9/08* (2013.01); *A61J 1/1468* (2015.05); *A61K 9/0019* (2013.01); *A61K 31/192* (2013.01); *A61K 47/02* (2013.01); *C08L 23/06* (2013.01); *C08L 2203/02* (2013.01); *C08L 2207/066* (2013.01)

(58) Field of Classification Search
None
See application file for complete search history.

(56) References Cited

U.S. PATENT DOCUMENTS 11,806,400 B2   11/2023   Pavliv et al.

FOREIGN PATENT DOCUMENTS

| CN | 105 796 489 A | 7/2016 | |
|---|---|---|---|
| WO | 2013/138628 A2 | 9/2013 | |
| WO | WO-2018025128 A1 * | 2/2018 | ........... A61K 31/192 |

OTHER PUBLICATIONS

Chapel Hill Gynecology, "Can you prevent early menopause?" ([retrieved from on-line website: https://chapelhillgynecology.com/can-you-prevent-early-menopause/, pp. 1-6, 2022]) (Year: 2022).*
CALDOLOR® Package Insert—Ref ID: 3928118 (May 9, 2016) 15 pgs.
CALDOLOR® Package Insert—Ref ID: 4465339 (Jul. 22, 2019) 16 pgs.
CALDOLOR® Package Insert—Ref ID: 4786643 (Apr. 28, 2021) 17 pgs.

(Continued)

*Primary Examiner* — Kyung S Chang
(74) *Attorney, Agent, or Firm* — Leydig, Voit & Mayer, Ltd.

(57) ABSTRACT

The invention relates to pharmaceutical compositions for parenteral administration comprising a) Ibuprofen or a pharmaceutically acceptable salt thereof, and b) a phosphate buffer.

19 Claims, 3 Drawing Sheets

(56) References Cited

OTHER PUBLICATIONS

European Patent Office, International Search Report in International Application No. PCT/EP2019/085138 (dated Feb. 18, 2020).
European Patent Office, Written Opinion in International Application No. PCT/EP2019/085138 (dated Feb. 18, 2020).
International Bureau of WIPO, International Preliminary Report on Patentability in International Application No. PCT/EP2019/085138 (dated Jun. 8, 2021).

* cited by examiner

PHARMACEUTICAL COMPOSITIONS FOR PARENTERAL ADMINISTRATION COMPRISING IBUPROFEN AND A PHOSPHATE BUFFER

CROSS-REFERENCE TO RELATED APPLICATIONS

This patent application is a continuation-in-part of co-pending International Application No. PCT/EP2019/085138, filed Dec. 13, 2019, which claims priority to European Patent Application No. 18212668.0, filed on Dec. 14, 2018, the disclosures of which are incorporated herein by reference in their entireties for all purposes.

FIELD OF THE INVENTION

The invention relates to Ibuprofen compositions for parenteral administration. In particular, the invention relates to a pharmaceutical composition comprising Ibuprofen or a pharmaceutically acceptable salt thereof and a phosphate buffer, said Ibuprofen compositions in a plastic container and medical uses thereof.

BACKGROUND OF THE INVENTION

Pain management and control of fever are key elements in post-operative patient care in hospitals. Several analgesics are available for oral, topical and parenteral application. Ibuprofen, due to its high efficacy and good safety profile, is a preferred option in this context. There is an emerging need for formulations that allow for short-term treatment by intravenous infusion.

Ibuprofen formulations for parenteral use are available in the form of concentrates. However, they require additional steps (e.g. a dilution step) in order to obtain solutions ready for injection.

There is a need for ready-to-use parenteral Ibuprofen formulations, which are easier to handle and allow for a convenient and safe application. Ideally, such a formulation is stored in a container that is also easy, convenient and safe to use, such as a plastic container.

SUMMARY OF THE INVENTION

The inventors have surprisingly found that an Ibuprofen formulation comprising relatively low amounts of a phosphate buffer and relatively low ratios phosphate buffer to Ibuprofen is stable and is more convenient for the patients compared to Ibuprofen formulations comprising higher amounts of phosphate buffer and higher ratios phosphate buffer to Ibuprofen. Advantageously, such a formulation can be stored in a plastic container.

Accordingly, in one aspect of the invention there is provided a pharmaceutical composition for parenteral administration comprising
   a) Ibuprofen or a pharmaceutically acceptable salt thereof, and
   b) a phosphate buffer,
wherein the concentration of Ibuprofen or a pharmaceutically acceptable salt thereof is in the range of 15-25 mmol/l, and wherein the molar ratio of phosphate to Ibuprofen is in the range of 0.2:1 to 0.5:1 or 0.35:1 to 0.37:1.

In a further aspect of the invention there is provided a pharmaceutical composition for parenteral administration comprising
   a) Ibuprofen or a pharmaceutically acceptable salt thereof, and
   b) a phosphate buffer,
wherein the concentration of Ibuprofen or a pharmaceutically acceptable salt thereof is in the range of 2-6 g/l, and wherein the molar ratio of phosphate to Ibuprofen is in the range of 0.2:1 to 0.5:1 or 0.35:1 to 0.37:1.

In yet a further aspect of the invention there is provided a pharmaceutical composition as defined herein in a plastic container.

In yet a further aspect of the invention there is provided a pharmaceutical composition as defined herein for use in the treatment of pain and/or reduction of fever.

Advantageously, the pharmaceutical composition of the invention is ready to use and thus easy to handle. The composition of the invention allows for a convenient and safe parenteral administration of Ibuprofen in the required dose regime to patients in need thereof. Advantageously, the pharmaceutical composition does neither require large amounts of the buffer, nor does it require the presence of excipients (e.g. amino acids) that may cause adsorption to a plastic container.

DETAILED DESCRIPTION OF THE INVENTION

The Pharmaceutical Composition

The pharmaceutical composition of the invention comprises Ibuprofen or a pharmaceutically acceptable salt thereof. Ibuprofen is known to a person skilled in the art. Preferred salts of Ibuprofen are sodium, potassium, lithium or ammonium salts. More preferred salts of Ibuprofen are sodium or potassium salt. A particularly preferred salt of Ibuprofen is sodium.

The pharmaceutical composition of the invention comprises a phosphate buffer. A person skilled in the art knows what a phosphate buffer is. Phosphate buffer as used herein refers to a buffer system comprising phosphate, hydrogenphosphate, dihydrogenphosphate and/or phosphoric acid.

The pharmaceutical composition of the invention comprises Ibuprofen or a pharmaceutically acceptable salt thereof and a phosphate buffer in a specific ratio. The molar ratio of phosphate to Ibuprofen as used herein refers to the ratio of moles Ibuprofen and pharmaceutically acceptable salts thereof to the sum of moles phosphate, hydrogenphosphate, dihydrogenphosphate and phosphoric acid. For example, in a composition comprising 19.4 mmol/l Ibuprofen or a pharmaceutically acceptable salt thereof, 5.0 mmol/l sodiumdihydrogenphosphate and 2.0 mmol/l disodiumhydrogenphosphate, the molar ratio of phosphate to Ibuprofen as used herein is 0.36.

If not indicated otherwise, the expression "mmol/l" refers to "mmol per l of the pharmaceutical composition". If not indicated otherwise, the expression "g/l" refers to "g per l of the pharmaceutical composition". In particular, the Ibuprofen and phosphate buffer concentrations given herein are based on the total volume of the pharmaceutical composition.

The pharmaceutical composition of the present invention is for parenteral administration. Preferably, the pharmaceutical composition is for intravenous administration.

Preferably, the molar ratio of phosphate to ibuprofen is in the range of 0.3:1 to 0.4:1. In some embodiments, the molar ratio of phosphate to Ibuprofen is in the range of 0.35:1 to 0.37:1.

Preferably, the phosphate buffer comprises trialkalimetalphosphates, dialkalimetalhydrogenphosphates and/or alkalimetaldihydrogenphosphates, more preferably dialkalimetalhydrogenphosphates and/or alkalimetaldihydrogenphosphates.

Alkali metal as used herein preferably refers to lithium (Li), sodium (Na) or potassium (K), more preferably sodium or potassium, particularly preferably sodium.

In a particularly preferred embodiment the phosphate buffer comprises sodiumdihydrogenphosphate and disodiumhydrogenphosphate. Sodiumdihydrogenphosphate can, for example, be used in the form of a hydrate, such as a dihydrate ($NaH_2PO_4 \times 2H_2O$). Disodiumhydrogenphosphate can, for example, be used in the form of a hydrate, such as a dodecahydrate ($Na_2HPO_4 \times 12H_2O$).

The amount of phosphate buffer in the pharmaceutical composition according to the invention is preferably adjusted in a way that it allows for the preparation of a storage stable. Typically, the concentration of the phosphate buffer is in the range of 4-10 mmol/l, preferably 5-9 mmol/l more preferably 6-8 mmol/l, based on the total volume of the pharmaceutical composition.

The pharmaceutical composition may comprise alkalizing and/or acidifying agents in order to adjust the pH of the pharmaceutical composition according to the requirements for solutions for parenteral administration. An alkalizing agent (particularly preferably sodium hydroxide) can also be used to solubilize Ibuprofen. In one embodiment the pharmaceutical composition comprises an alkalizing agent. Preferably, the alkalizing agent is selected from the group consisting of sodium carbonate, potassium carbonate, sodium bicarbonate, potassium bicarbonate, sodium hydroxide and potassium hydroxide, preferably sodium hydroxide. In another embodiment the pharmaceutical composition comprises an acidifying agent, preferably hydrochloric acid.

Preferably, the pH of the pharmaceutical composition of the present invention is in the range of 6.5 to 8.2, more preferably 7.2-8.0, even more preferably 7.4-7.8.

Typically, the concentration of Ibuprofen or a pharmaceutically acceptable salt thereof is in the range of 2-6 g/l, preferably 3-5 g/l, more preferably 3.5-4.5 g/l, based on the total volume of the pharmaceutical composition. Also typically, the concentration of the Ibuprofen or the pharmaceutically acceptable salt thereof is in the range of 15-25 mmol/l, preferably 17-23 mmol/l more preferably 19-20 mmol/l, based on the total volume of the pharmaceutical composition.

Preferably, the pharmaceutical composition comprises a tonicity modifying agent in order to adjust the tonicity of the pharmaceutical composition according to the requirements for solutions for parenteral administration. Suitable tonicity modifying agents are known by a person skilled in the art. Preferred tonicity modifying agents are glycerol, propylene glycol, sorbitol, mannitol, dextrose, lactose, potassium chloride or sodium chloride. More preferred tonicity agents are glycerol, propylene glycol, or sodium chloride. A particularly preferred tonicity agent is sodium chloride.

In one embodiment the pharmaceutical composition does not comprise an amino acid or a salt thereof and/or an organic amine or a salt thereof.

Preferably, the pharmaceutical composition is an aqueous composition. Generally, an aqueous composition is a composition comprising water. In such preferred embodiments, the water content of the pharmaceutical composition is typically in the range of 50-100 volume %, more preferably 80-100 volume %, even more preferably 90-100 volume %, particularly preferably 95-100 volume %, for example 99-100 volume %, based on the total volume of the pharmaceutical composition. Particularly preferably, water is used as the sole solvent. Preferably the water comprised in the pharmaceutical composition is microbiologically purified water capable of being used for parenteral purposes, such as water for injection (WFI).

Preferably, the pharmaceutical composition of the present invention is a ready-to-use composition. Ready-to-use composition as used herein refers to a composition which does not need to be further diluted before administration. It can be administered as it is.

The pharmaceutical composition of the invention is typically a clear and colorless to pale yellowish solution with good storage stability. It can, for example, be stored at 25° C. for at least 24 months.

The Container

In one aspect the invention provides a pharmaceutical composition in a plastic container.

Preferably, the plastic container is a plastic bottle, a plastic bag or a plastic vial, even more preferably a plastic bottle or a plastic bag, particularly preferably a plastic bottle. Such plastic containers are stable and easy to handle, and allows for easy transport and administration.

Preferably, the plastic container comprises polymers selected form the group of polyethylene, polypropylene, polybutylene, polyisoprene, polystyrene and polyvinylchloride, more preferably polyethylene, even more preferably low density polyethylene (LDPE). The polymers may be present in the form of homo-polymers or co-polymers. Co-polymers as used herein include random- and block-copolymers.

The plastic container may comprise one or more layers, preferably 1-3 layers, more preferably 1 layer. In the case the plastic container comprises more layers the layers may be identical of different regarding their polymer composition.

Preferably, the plastic container comprises a plastic cap. Preferably, the plastic cap comprises polyethylene, polypropylene, polyvinylchloride or mixtures or copolymers thereof, more preferably polypropylene or copolymers thereof.

Preferably, the plastic container has a volume in the range of 25-1000 ml, preferably 50-500 ml, more preferably 50-150 ml, particularly preferably 100 ml.

Typically, the pharmaceutical composition in the plastic container has a storage stability of at least 6 months, preferably at least 12 months, more preferably at least 24 months at 25° C.

Preparation

The pharmaceutical compositions of the invention can be prepared employing processes known by a person skilled in the art. For example, the pharmaceutical composition can be prepared by a) mixing its components and b) optionally pH adjustment. In particularly preferred embodiments, where the pharmaceutical composition is in a plastic container and sterilized, the manufacturing process may, for example, comprise the following the steps:

a) mixing the components of the pharmaceutical composition;
b) optionally pH adjustment;
c) optionally filtration;
d) filling of the plastic container;
e) sterilization.

The filtration can, for example, be done using filters having pore sizes in the range of 0.2-0.6 µm, capable of removing microbiological contaminations. In particularly preferred embodiments, the filtration comprises two filtration steps.

The filling of the plastic container is done using filling techniques known in the art. In preferred embodiments, where the plastic container is a LDPE container, the filling can, for example, be done using a Blow-Fill-Seal technology.

Preferably, the pharmaceutical composition in a plastic container is sterilized in order to provide a storage stable composition for parenteral administration. Typical sterilization methods include sterilization by dry heat, moist heat, irradiation and gases. Preferably, heat sterilization is used. More preferably, moist heat sterilization is used. Particularly preferably, moist heat sterilization with overheated water as sterilizing medium is used. The temperature of the overheated water is generally at least 100° C., preferably at least 110° C., more preferably at least 111° C. In a preferred embodiment, the temperature of the overheated water is about 111° C. In another embodiment, the temperature of the overheated water is about 121° C.

Use

According to one aspect of the invention the pharmaceutical composition as defined herein is for use in the treatment of pain and/or reduction of fever. Preferably, the treatment is a short-term treatment. More preferably, the treatment is a short-term acute treatment. Preferably, the pain is a mild to moderate pain. In one embodiment the pharmaceutical composition is for use in the treatment of pain, preferably for use in the short-term treatment of mild to moderate pain. In another embodiment the pharmaceutical composition is for use in the reduction of fever.

EMBODIMENTS

1. Pharmaceutical composition for parenteral administration comprising
   a) Ibuprofen or a pharmaceutically acceptable salt thereof, and
   b) a phosphate buffer,
   wherein the concentration of Ibuprofen or a pharmaceutically acceptable salt thereof is in the range of 15-25 mmol/l, and wherein the molar ratio of phosphate to Ibuprofen is in the range of 0.2:1 to 0.5:1, preferably 0.3:1 to 0.4:1, more preferably 0.35:1 to 0.37:1.

2. Pharmaceutical composition for parenteral administration comprising
   a) Ibuprofen or a pharmaceutically acceptable salt thereof, and
   b) a phosphate buffer,
   wherein the concentration of Ibuprofen or a pharmaceutically acceptable salt thereof is in the range of 2-6 g/l, and wherein the molar ratio of phosphate to Ibuprofen is in the range of 0.2:1 to 0.5:1, preferably 0.3:1 to 0.4:1, more preferably or 0.35:1 to 0.37:1.

3. Pharmaceutical composition according to any of the preceding embodiments, wherein the concentration of Ibuprofen or a pharmaceutically acceptable salt thereof is in the range of 17-22 mmol/l, preferably 18-21 mmol/l, more preferably 19-20 mmol/l.

4. Pharmaceutical composition according to any of the preceding embodiments, wherein the concentration of Ibuprofen or a pharmaceutically acceptable salt thereof is in the range of 3-5 g/I, more preferably 3.5-4.5 g/I.

5. Pharmaceutical composition according to any of the preceding embodiments, wherein the phosphate buffer comprises a trialkalimetalphosphate, a dialkalimetalhydrogenphosphate and/or an alkalimetaldihydrogenphosphate, preferably comprises a dialkalimetalhydrogenphosphate and/or an alkalimetaldihydrogenphosphate.

6. Pharmaceutical composition according to any of the preceding embodiments, wherein the alkali metal is sodium or potassium, preferably sodium.

7. Pharmaceutical composition according to any of the preceding embodiments, wherein the phosphate buffer comprises sodiumdihydrogenphosphate and/or disodiumhydrogenphosphate, preferably sodiumdihydrogenphosphate and disodiumhydrogenphosphate.

8. Pharmaceutical composition according to any of the preceding embodiments, wherein the concentration of the phosphate buffer is in the range of 4-10 mmol/l, preferably 5-9 mmol/l, more preferably 6-8 mmol/l.

9. Pharmaceutical composition according to any of the preceding embodiments, wherein the pH of the composition is in the range of 6.5 to 8.2, preferably 7.2-8.0, more preferably 7.4-7.8.

10. Pharmaceutical composition according to any of the preceding embodiments further comprising a tonicity modifying agent.

11. Pharmaceutical composition according to the preceding embodiment, wherein the tonicity modifying agent is selected from the group consisting of glycerol, propylene glycol, sorbitol, mannitol, dextrose, lactose, potassium chloride and sodium chloride, preferably is glycerol, propylene glycol or sodium chloride, more preferably is sodium chloride.

12. Pharmaceutical composition according to any of the preceding embodiments further comprising an alkalizing agent.

13. Pharmaceutical composition according to the preceding embodiment, wherein the alkalizing agent is selected from the group consisting of sodium carbonate, potassium carbonate, sodium bicarbonate, potassium bicarbonate, sodium hydroxide and potassium hydroxide, preferably is sodium hydroxide.

14. Pharmaceutical composition according to any of the preceding embodiments further comprising an acidifying agent.

15. Pharmaceutical composition according to the preceding embodiment, wherein the acidifying agent is hydrochloric acid.

16. Pharmaceutical composition according to any of the preceding embodiments, which is a liquid composition.

17. Pharmaceutical composition according to any of the preceding embodiments, which is an aqueous composition.

18. Pharmaceutical composition according to any of the preceding embodiments, which is an aqueous liquid composition.

19. Pharmaceutical composition according to any of the preceding embodiments, which is a ready-to-use composition.

20. Pharmaceutical composition according to any of the preceding embodiments comprising
    a) 19.4 mmol/l Ibuprofen or a pharmaceutically acceptable salt thereof,
    b) 5.0 mmol/l sodiumdihydrogenphosphate, and
    c) 2.0 mmol/l disodiumhydrogenphosphate,
    wherein the composition further comprises sodium chloride, and wherein the composition has a pH in the range of 7.2-8.0, preferably 7.4-7.8.

21. Pharmaceutical composition according to any of the preceding embodiments comprising
    a) 4.0 g/l Ibuprofen or a pharmaceutically acceptable salt thereof,
    b) 5.0 mmol/l sodiumdihydrogenphosphate, and
    c) 2.0 mmol/l disodiumhydrogenphosphate,
    wherein the composition further comprises sodium chloride, and wherein the composition has a pH in the range of 7.2-8.0, preferably 7.4-7.8.

22. Pharmaceutical composition according to any of the preceding embodiments, wherein the composition does not contain arginine, lysine or a salt thereof.

23. Pharmaceutical composition according to any of the preceding embodiments, wherein the composition does not contain an amino acid or a salt thereof.

24. Pharmaceutical composition according to any of the preceding embodiments, wherein the composition does not contain tromethamine or a salt thereof.

25. Pharmaceutical composition according to any of the preceding embodiments, wherein the composition does not contain an organic amine or a salt thereof.

26. Pharmaceutical composition according to any of the preceding embodiments, which is in a plastic container.

27. Pharmaceutical composition for parenteral administration in a container comprising
    a) Ibuprofen or a pharmaceutically acceptable salt thereof, and
    b) a phosphate buffer,
    wherein the concentration of Ibuprofen or a pharmaceutically acceptable salt thereof is in the range of 15-25 mmol/l, wherein the molar ratio of phosphate to Ibuprofen is in the range of 0.2:1 to 0.5:1 or 0.35:1 to 0.37:1.

28. Pharmaceutical composition for parenteral administration in a container comprising
    a) Ibuprofen or a pharmaceutically acceptable salt thereof, and
    b) a phosphate buffer,
    wherein the concentration of Ibuprofen or a pharmaceutically acceptable salt thereof is in the range of 2-6 g/l, wherein the molar ratio of phosphate to Ibuprofen is in the range of 0.2:1 to 0.5:1 or 0.35:1 to 0.37:1.

29. Pharmaceutical composition according to any of embodiments 26 to 28, wherein the plastic container is a plastic bottle, a plastic bag or a plastic vial, more preferably a plastic bottle or a plastic bag, particularly preferably a plastic bottle.

30. Pharmaceutical composition according to embodiment 29, wherein the plastic comprises polyethylene, polypropylene, polybutylene, polyisoprene, polystyrene, polyvinylchloride or mixtures or copolymers thereof, preferably polyethylene, more preferably low density polyethylene (LDPE).

31. Pharmaceutical composition according to embodiment 29 or 30, wherein the plastic comprises polyethylene, polypropylene, polyvinylchloride or mixtures or copolymers thereof, preferably polypropylene or copolymers thereof.

32. Pharmaceutical composition according to any of embodiments 26 to 31, wherein the plastic container has a volume in the range of 25-500 ml, preferably 50-150 ml, more preferably 80-120 ml, particularly preferably 100 ml.

33. Pharmaceutical composition according to any of embodiments 26 to 32, wherein the plastic container comprises a plastic cap, preferably a polypropylene cap.

34. Pharmaceutical composition according to any of the preceding embodiments, wherein the composition is sterilized, preferably heat sterilized, more preferably moist heat sterilized.

35. Aqueous pharmaceutical composition according to any of the preceding embodiments comprising
    a) 19.4 mmol/l Ibuprofen or a pharmaceutically acceptable salt thereof,
    b) 5.0 mmol/l sodium dihydrogenphosphate, and
    c) 2.0 mmol/l disodiumhydrogenphosphate,
    wherein the composition further comprises sodium chloride, wherein the composition has a pH in the range of 7.2-8.0 (preferably 7.4-7.8), wherein the plastic container is a polyethylene container having a volume of 100 ml comprising a polypropylene cap, and wherein the composition is sterilized.

36. Aqueous pharmaceutical composition according to any of the preceding embodiments comprising
    a) 4.0 g/l Ibuprofen or a pharmaceutically acceptable salt thereof,
    b) 5.0 mmol/l sodium dihydrogenphosphate, and
    c) 2.0 mmol/l disodiumhydrogenphosphate,
    wherein the composition further comprises sodium chloride, wherein the composition has a pH in the range of 7.2-8.0 (preferably 7.4-7.8), wherein the plastic container is a polyethylene container having a volume of 100 ml comprising a polypropylene cap, and wherein the composition is sterilized.

37. Pharmaceutical composition according to any of the preceding embodiments, which is a ready-to-use composition.

38. Pharmaceutical composition as defined in any of the preceding embodiments for use in the treatment of pain and/or reduction of fever.

The invention is further illustrated by the following examples without being limited thereby.

EXAMPLES

Example 1

Preparation of a Pharmaceutical Composition

At 60-65° sodium hydroxide solution was added to WFI. Subsequently, Ibuprofen powder was added. After complete dissolution of the Ibuprofen the solution was cooled to 50° C. followed by the addition of sodium chloride and phosphate buffer substances. The pH of the solution was adjusted to pH=7.4-7.8. The solution was filtered in a two-step filtration process employing a 0.6 μm filter in the first step and a 0.2 μm filter in a second step.

The composition comprises the following ingredients in a total volume of 5000 L:

| Substance | Amount per l | Amount [mmol/l] |
|---|---|---|
| WFI | ad 100% | ad 100% |
| Ibuprofen | 4.0 g | 19.4 |
| NaCl | 7.5 g | 128.3 |
| $NaH_2PO_4 \times 2H_2O$ | 0.780 g | 5.0 |
| $Na_2HPO_4 \times 12H_2O$ | 0.716 g | 2.0 |
| NaOH 5M | 4.8 ml | 24.0 |
| NaOH 1M (pH adjustment) | q.s. | q.s. |
| HCl 1M (pH adjustment) | q.s. | q.s. |

Filling and sterilization: Polyethylene containers (KabiPac®) were filled with the pharmaceutical composition and sealed. The filled containers were sterilized by autoclaving 111° C.).

Example 2

Stability of the Pharmaceutical Composition a) Oxygen Sensitivity

Two formulations having the composition as shown in example 1 were prepared. One formulation was aerated and one stored under nitrogen protection. Both formulations showed comparable results with respect to appearance of the solutions, degree of coloration, pH, visible- and sub-visible particles, osmolality and impurities. All results fulfilled the acceptance criteria of solutions for parenteral administration with respect to all parameters investigated.

b) pH Stability/Adsorption Behavior

A pharmaceutical composition (pH=7.4-7.8) in a polyethylene container (KabiPac® Fresenius Kabi) as descried in example 1 was prepared. The pH remained stable over time. The formulation did not show adsorption behavior after 6 months storage.

c) Stability, Including Heat Stability

The formulation having the composition as described in example 1 was tested for stability in a low density polyethylene container (KabiPac®, Fresenius Kabi) at 60° C. for 2 and 4 weeks and at 40° C. and 25° C. for 3 and 6 months. The pH stability was tested at pH=6.5, 7.1 and 7.4. No pH changes were detectable over the whole stability testing period.

d) Storage Stability I

Formulations having the composition as described in example 1 in (Kabipac®) were prepared.

Part I: Degradation Products

The formulations were stored under different conditions for 3 and 6 months, respectively.

Storage conditions: 25° C.±2° C./40%±5% RH
30° C.±2° C./35%±5% RH
40° C.±2° C./≤25% RH The formulations were stable over the tested period. For example, the amount of total degradation products was <0.1% in all cases (i.e. under all tested storage conditions after 3 and 6 months, respectively).

Part II: Ion Content

Samples having the composition as described in example 1 were prepared. 100 ml of the resulting pharmaceutical composition were filled in KabiPac® bottles and glass bottles having a hydrolysis class (HK) HK1 and HK2, respectively.

Sterilization of KabiPac® was done at 111° C. Sterilization of glass bottles was done at 121° C. as appropriate for glass packaging materials.

Storage Conditions:

| Storage Conditions | KabiPac | 100 mL Glass Bottle HK1 | 100 mL Glass Bottle HK2 |
|---|---|---|---|
| T0 not autoclaved | 2 | 2 | 2 |
| T0 autoclaved | 2 | 2 | 2 |
| 80° C.-1 week | 2 | 2 | 2 |

Figure 1A:
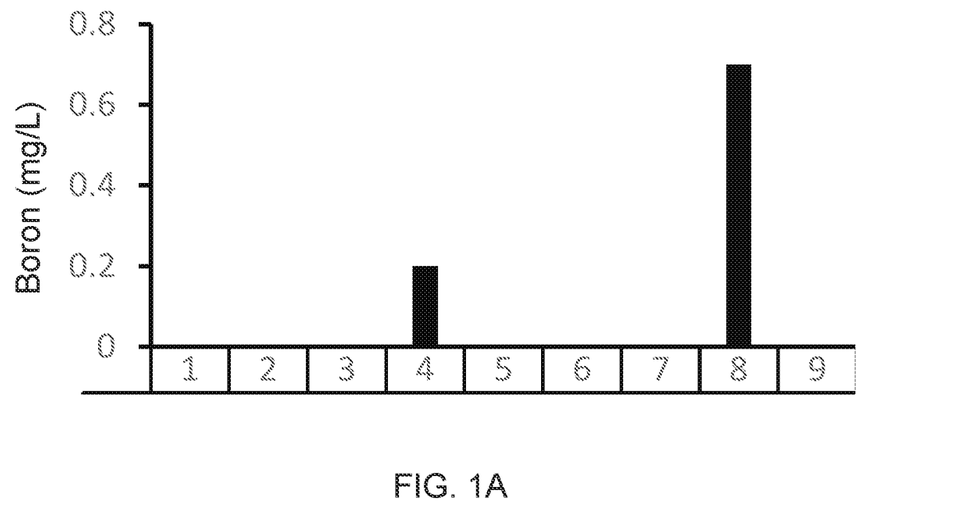
FIGS. 1A-1F illustrate the amount of Boron (FIG. 1A), Aluminum (FIG. 1B), Silicon (FIG. 1C), Magnesium (FIG. 1D), Barium (FIG. 1E), and Calcium (FIG. 1F) as determined by induced coupled plasma mass spectrometry (ICP-MS) present in an aqueous pharmaceutical composition comprising 19.4 mM ibuprofen, 7 mM phosphate buffer, pH 7.4-7.8, contained within a plastic bottle (KabiPac) or a glass bottle having a hydrolysis class 1 (HK1) or hydrolysis class 2 (HK2) as a function of sterilization (autoclaving at 111° C. for KabiPac or at 121° C. for Glass HK1 and Glass HK2) and storage duration time (T), as follows:
   1) KabiPac, not autoclaved, T=0
   2) KabiPac, autoclaved, T=0
   3) Glass HK1, not autoclaved, T=0
   4) Glass HK1, autoclaved, T=0
   5) Glass HK2, not autoclaved, T=0
   6) Glass HK2, autoclaved, T=0
   7) KabiPac, autoclaved, T=1 week at 80° C.
   8) Glass HK1, autoclaved, T=1 week at 80° C.
   9) Glass HK2, autoclaved, T=1 week at 80° C.
Figure 1B:
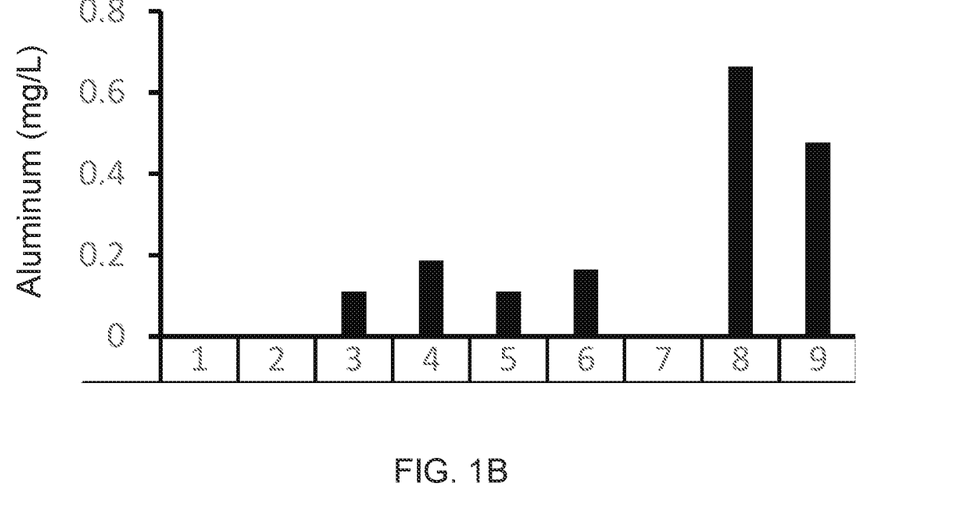
Figure 1C:
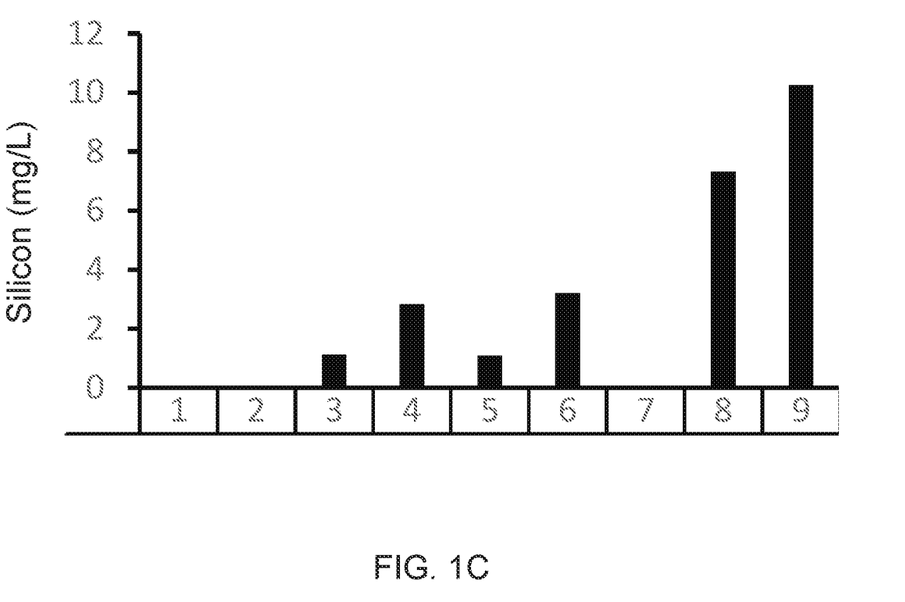
Figure 1D:
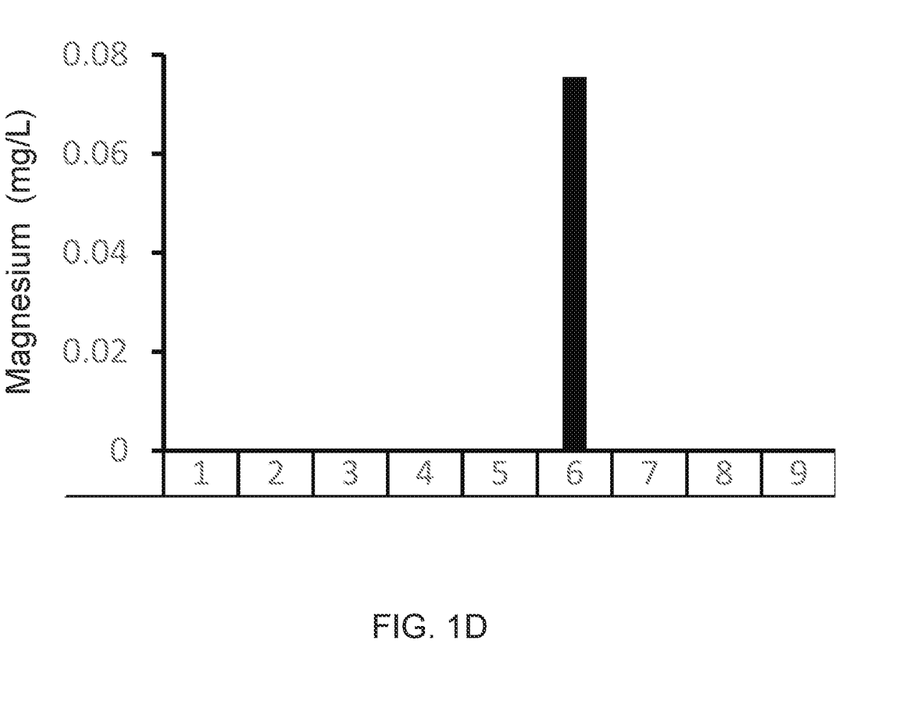
Figure 1E:
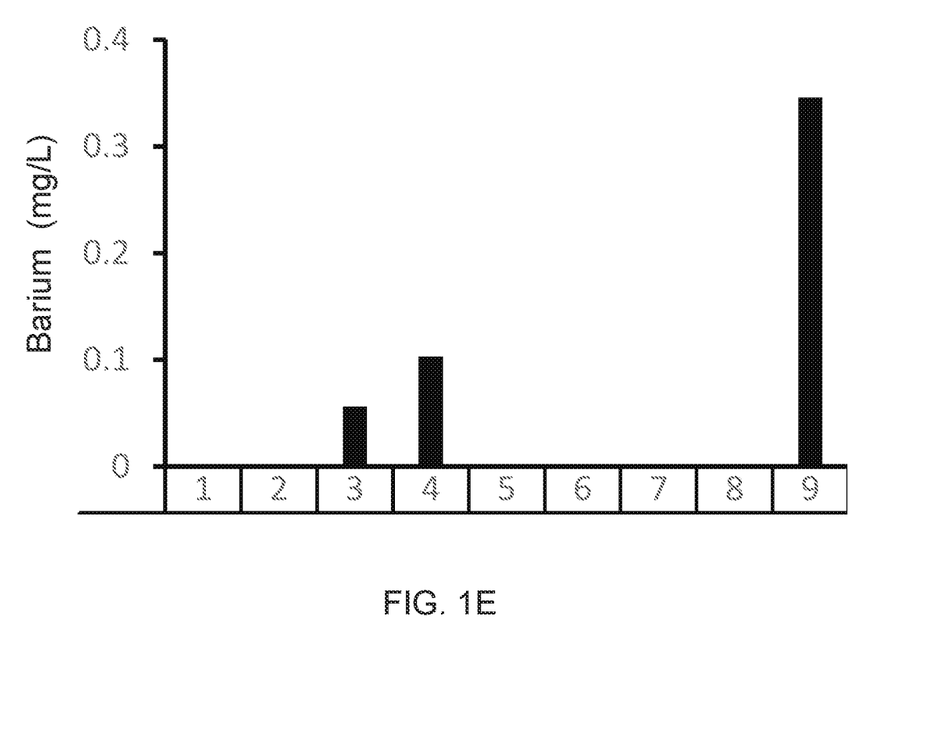
Figure 1F:
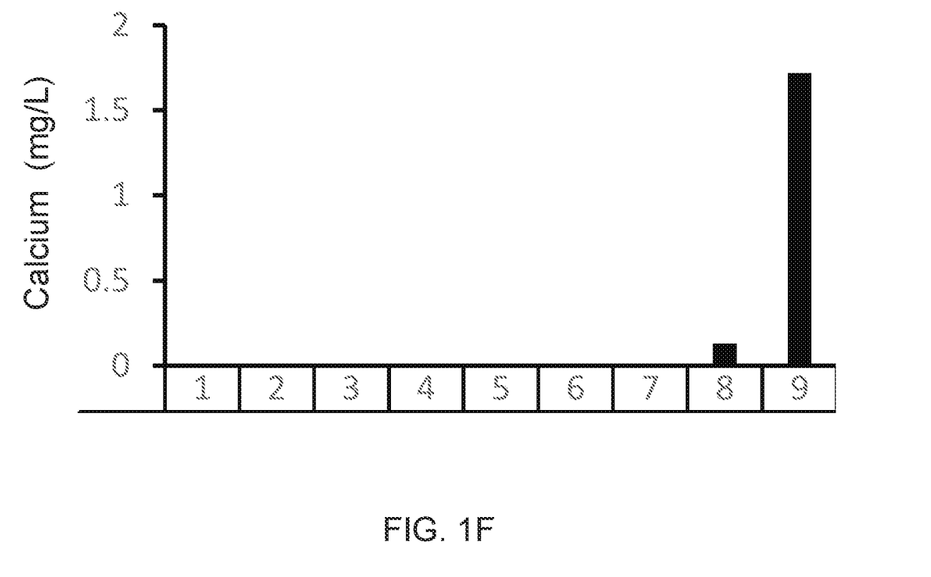

The analysis of samples was performed by induced coupled plasma mass spectrometry (IC-MS). The results (table 1 and FIGS. 1A-1F) clearly demonstrate the higher storage stability of the KabiPac® container in comparison to the two different glass containers used in the experiment illustrated by the higher leakage of Aluminum-, Boron-, Silicon-, Barium-, Magnesium- and Calcium ions from the glass container.

TABLE 1

ICP-MS results (example 1 d) part II)

| Sample | B mg/L | Na mg/L | Mg mg/L | Al mg/L | Si mg/L | K mg/L | Ca mg/L |
|---|---|---|---|---|---|---|---|
| KabiPac T = 0 not autoclaved | <0.05 | 3922 | <0.05 | <0.1 | <0.1 | 0.8 | <0.1 |
| KabiPac T = autoclaved | <0.05 | 4167 | <0.05 | <0.1 | <0.1 | 1.0 | <0.1 |
| Glass HK1 T = 0 not autoclaved | <0.05 | 4301 | <0.05 | 0.1 | 1.1 | 1.1 | <0.1 |
| Glass HK1 T = 0 autoclaved | 0.20 | 4324 | <0.05 | 0.2 | 2.8 | 1.2 | <0.1 |
| Glass HK2 T = 0 not autoclaved | <0.05 | 4577 | <0.05 | 0.1 | 1.1 | 1.4 | <0.1 |
| Glass HK2 T = 0 autoclaved | <0.05 | 4412 | 0.08 | 0.2 | 3.2 | 1.3 | <0.1 |
| KabiPac T = 1 w 80° C. | <0.05 | 4851 | <0.05 | <0.1 | <0.1 | 1.9 | <0.1 |
| Glass HK1 T = 1 w 80° C. | 0.70 | 4838 | <0.05 | 0.66 | 7.3 | 2.1 | 0.1 |
| Glass HK2 T = 1 w 80° C. | <0.05 | 4903 | 0.26 | 0.48 | 10.3 | 2.1 | 1.7 |

| | Ti | V | Cr | Fe | Ni | Zn | Zr | Ba |
|---|---|---|---|---|---|---|---|---|

TABLE 1-continued

ICP-MS results (example 1 d) part II)

| Sample | mg/L | mg/L | mg/L | mg/L | mg/L | mg/L | mg/L | mg/L |
|---|---|---|---|---|---|---|---|---|
| KabiPac T = 0 not autoclaved | <0.05 | <0.01 | <0.01 | <0.01 | <0.01 | <0.1 | <0.01 | <0.01 |
| KabiPac T = autoclaved | <0.05 | <0.01 | <0.01 | <0.01 | <0.01 | <0.1 | <0.01 | <0.01 |
| Glass HK1 T = 0 not autoclaved | <0.05 | <0.01 | <0.01 | <0.01 | <0.01 | <0.1 | <0.01 | 0.06 |
| Glass HK1 T = 0 autoclaved | <0.05 | <0.01 | <0.01 | <0.01 | <0.01 | <0.1 | <0.01 | 0.10 |
| Glass HK2 T = 0 not autoclaved | <0.05 | <0.01 | <0.01 | <0.01 | <0.01 | <0.1 | <0.01 | <0.01 |
| Glass HK2 T = 0 autoclaved | <0.05 | <0.01 | <0.01 | <0.01 | <0.01 | <0.1 | <0.01 | <0.01 |
| KabiPac T = 1 w 80° C. | <0.05 | <0.01 | <0.01 | <0.01 | <0.01 | <0.1 | <0.01 | <0.01 |
| Glass HK1 T = 1 w 80° C. | <0.05 | <0.01 | <0.01 | <0.01 | <0.01 | <0.1 | <0.01 | 0.35 |
| Glass HK2 T = 1 w 80° C. | <0.05 | <0.01 | <0.01 | <0.01 | <0.01 | <0.1 | <0.01 | <0.01 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A ready-to-use pharmaceutical composition for parenteral administration comprising
   a) 15-25 mmol/L of Ibuprofen or a pharmaceutically acceptable salt thereof, and
   b) a phosphate buffer,
   wherein the phosphate buffer and Ibuprofen are present in a molar ratio of 0.3:1 to 0.4:1, the composition has a pH of 6.5 to 8.2, and the composition is sterile and has a storage stability of at least 12 months at 25° C.

2. A ready-to-use pharmaceutical composition for parenteral administration comprising
   a) 2-6 g/L of Ibuprofen or a pharmaceutically acceptable salt thereof, and
   b) a phosphate buffer,
   wherein the phosphate buffer and Ibuprofen are present in a molar ratio of 0.3:1 to 0.4:1 the composition has a pH of 6.5 to 8.2, and the composition is sterile and has a storage stability of at least 12 months at 25° C.

3. The pharmaceutical composition according to claim 1, wherein the phosphate buffer comprises a trialkalimetalphosphate, a dialkalimetalhydrogenphosphate and/or an alkalimetaldihydrogenphosphate.

4. The pharmaceutical composition according to claim 1, wherein the pH of the composition is 7.2 to 8.0.

5. The pharmaceutical composition according to claim 1 further comprising a tonicity modifying agent.

6. The pharmaceutical composition according to claim 1, which is provided in a plastic container.

7. A ready-to-use pharmaceutical composition for parenteral administration in a plastic container comprising
   a) 15-25 mmol/L of Ibuprofen or a pharmaceutically acceptable salt thereof, and
   b) a phosphate buffer,
   wherein the phosphate buffer and Ibuprofen are present in a molar ratio of 0.3:1 to 0.4:1 the composition has a pH of 6.5 to 8.2, and the composition is sterile and has a storage stability of at least 12 months at 25° C.

8. The pharmaceutical composition according to claim 7, wherein the plastic container is a plastic bottle, a plastic bag or a plastic vial.

9. The pharmaceutical composition according to claim 8, wherein the plastic comprises polyethylene, polypropylene, polybutylene, polyisoprene, polystyrene, polyvinylchloride or mixtures or copolymers thereof.

10. The pharmaceutical composition according to claim 7, wherein the plastic container has a volume in the range of 25-500 ml.

11. The pharmaceutical composition according to claim 7, wherein the composition is heat sterilized.

12. The pharmaceutical composition according to claim 7, which is an aqueous composition.

13. The pharmaceutical composition according to claim 1, wherein the molar ratio of phosphate buffer to Ibuprofen is 0.35:1 to 0.37:1.

14. The pharmaceutical composition according to claim 2, wherein the molar ratio of phosphate buffer to Ibuprofen is 0.35:1 to 0.37:1.

15. The pharmaceutical composition according to claim 7, wherein the molar ratio of phosphate buffer to Ibuprofen is 0.35:1 to 0.37:1.

16. The pharmaceutical composition according to claim 1, wherein the pH of the composition is 7.4 to 7.8.

17. The pharmaceutical composition according to claim 2, wherein the pH of the composition is 7.4 to 7.8.

18. The pharmaceutical composition according to claim 7, wherein the pH of the composition is 7.4 to 7.8.

19. The pharmaceutical composition according to claim 9, wherein the plastic comprises low density polyethylene (LDPE).

* * * * *